United States Patent

Chang

[11] Patent Number: 5,449,913
[45] Date of Patent: Sep. 12, 1995

[54] APPARATUS FOR PRODUCING ATTENUATION SCAN

[76] Inventor: Wei Chang, 2445 Tanglewood Dr., Lisle, Ill. 60532

[21] Appl. No.: 147,807
[22] Filed: Nov. 3, 1993
[51] Int. Cl.⁶ .............................................. G01T 1/166
[52] U.S. Cl. ................................................ 250/363.04
[58] Field of Search .................................... 250/363.04

[56] References Cited

U.S. PATENT DOCUMENTS

| | | | |
|---|---|---|---|
| 3,484,604 | 12/1969 | Matsuda et al. | 378/24 |
| 4,638,499 | 1/1987 | Eberhard et al. | 378/7 |
| 4,670,657 | 6/1987 | Hawman et al. | 250/505.1 |
| 4,788,429 | 11/1988 | Wilson | 250/363.02 |
| 4,831,261 | 5/1989 | Genna et al. | 250/373.01 |
| 5,075,554 | 12/1991 | Yunker et al. | 250/363.08 |
| 5,155,365 | 10/1992 | Cann et al. | 250/363.02 |
| 5,210,421 | 5/1993 | Gullberg et al. | 250/363.04 |

FOREIGN PATENT DOCUMENTS 58-92974  6/1983  Japan .................... 250/363.04

Primary Examiner—Constantine Hannaher
Attorney, Agent, or Firm—Pearson & Pearson

[57] ABSTRACT

Apparatus for producing attenuation data for compensating a radionuclide emission imaging system. A single photon emission computed tomography (SPECT) system includes a radiation source disposed across the field of view from a detector portion and offset from a diameter through the center of the field of view intersecting a center of the detector portion. The radiation source and detector thereby define an asymmetrical radiation pattern that enlarges an attenuation field of view to provide a more thorough sampling of an object in the field of view.

20 Claims, 3 Drawing Sheets

APPARATUS FOR PRODUCING ATTENUATION SCAN

BACKGROUND OF THE INVENTION

1. Field of the Invention

This invention generally relates to radionuclide emission imaging and more specifically to improving quantitative information concerning physiological processes obtained by such imaging.

2. Description of Related Art

The use of radionuclide emission imaging for obtaining tomographic images is well known. These images visually present the distribution of a radionuclide tracer through a region of interest, typically in a human where regions of interest include the brain, heart, lungs, liver and other organs. This distribution of the tracer and associated compound models some physiological function such as blood flow or glucose metabolism in the region of interest.

Single photon emission computed tomographic (SPECT) imaging is one example of radionuclide emission imaging in which a collimator defines a plurality of photon flight paths to each of one or more photon detectors. The photon detectors receive photons emitted from the tracer in the patient along the various flight paths. Corresponding electronics analyze the received photons and assign to each flight path a vector having an intensity value that depends upon the number of photons received along that flight path. Processing these vectors by known reconstruction algorithms yields the final image.

In actual practice, SPECT and other radionuclide emission imaging systems must account for a number of other factors that can influence the accuracy of the final image and hence the information about the selected physiological process. This invention is directed to one such factor, namely the attenuation of photon energy as each photon travels from the emitting tracer nucleus through an object such as the patient's body to the collimator and detector. An accurate knowledge of this attenuation enables the intensity value associated with each vector to be compensated whereby the accuracy of the distribution can be translated into accurate absolute information, rather than just relative information.

One approach for determining attenuation involves using statistical models and assuming a substantially uniform density through the object or body being imaged. In some applications this approach provides reasonably accurate corrections. However, when the area being imaged includes significant density changes, as by organs of different densities and by organs and bones, this approach is not sufficiently accurate to provide accurate quantitative information.

U.S. Pat. No. 5,155,365 to Cann et al. for an Emission-Transmission Imaging System Using Single Energy and Dual Energy Transmission and Radionuclide Emission Data describes two other prior art approaches for obtaining photon attenuation emission. One involves the production of a computed tomography (CT) image using X-ray emissions independently of the emission image. Another involves the use of a radionuclide transmission source to obtain total length attenuation information. However, in each the attenuation measurement is made either before or after the emission image and in some situations at different locations. This complicates the correlation of the attenuation information with the emission image. The Cann et al. reference also discloses the use of a dual-energy X-ray source and a three-energy level detector system. The detector system discriminates among two discrete photon energy levels from the X-ray source and the energy level of photons emitted from the radionuclide tracer. This approach enables emission and attenuation to be obtained simultaneously and minimizes the problems correlating the attenuation and emission image data. However, the addition of a dual-energy X-ray apparatus effectively limits the application of this approach to single head SPECT systems. The apparatus is also more complex and expensive to manufacture.

U.S. Pat. No. 5,210,421 to Gullberg et al. for Simultaneous Transmission and Emission Converging Tomography discloses a three-head SPECT apparatus. In this patent, each head includes a photon detector system. A gantry supports the heads with equiangular spacing (e.g., 120° for a three-head apparatus) and rotates those heads about the patient in order to provide improved sampling within a field of view that is a circle lying within and circumscribed by the heads. This apparatus obtains attenuation data by disposing a collimated radiation source diametrically across the field of view from one of the heads. The detectors in this head can discriminate between photons emitted from the radiation source and from the radionuclide tracer within the body. The flight paths for detected photons from the radiation source to the surface of the detector define a radiation fan that lies within an isosceles triangle in the image plane. The base of this triangle is located at the plane of the detectors and the apex of the triangle is located at the radiation source located midway between the other two detector heads. The physical construction of typical multiple head SPECT imaging apparatus limits the spread of the radiation fans (i.e., the angle at the apex of the triangle). Consequently the photons from the radiation source do not provide full and even sampling through objects that fill substantial portions of the field of view, as will be described. Moreover, reliance on the ability of the photon detectors to discriminate between photon energies to separate emission and transmission photons, complicates the apparatus and must be taken into account each time a different tracer is utilized.

SUMMARY

Therefore, it is an object of this invention to provide radionuclide emission imaging apparatus that provides improved photon attenuation data.

Another object of this invention is to provide improved photon attenuation data for single photon emission computed tomographic imaging apparatus.

Yet another object of this invention is to provide improved photon attenuation data for single photon emission computed tomographic imaging apparatus with multiple detector heads.

Still another object of this invention is to provide improved photon attenuation data for single photon emission computed tomographic imaging apparatus without unduly increasing the complexity and cost of the apparatus and minimizing any complications in the use of the apparatus.

In accordance with this invention, a radionuclide emission imaging system produces an image of an object located in a field of view defined about an axis. A support rotates a detector about the field of view and a radiation source directs photons toward the detector through the field of view. The source is positioned remotely from a diameter through the center of the field of view and of the detector whereby the radiation fan from the radiation source to the detector is non-symmetrical.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
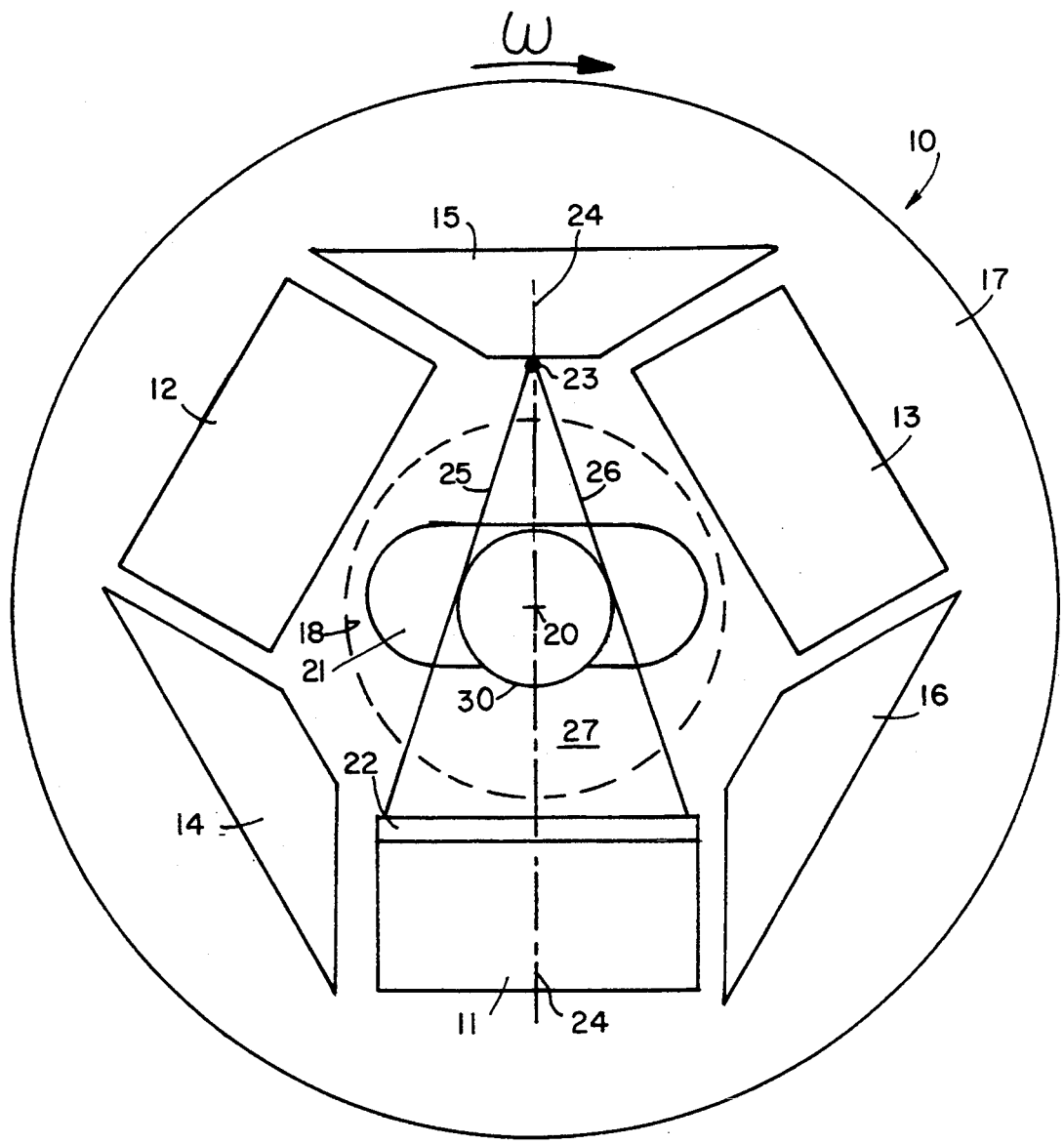
FIG. 1 depicts, in schematic form, a three-head single photon emission computed tomographic imaging apparatus with a prior art attenuation apparatus.
Figure 2:
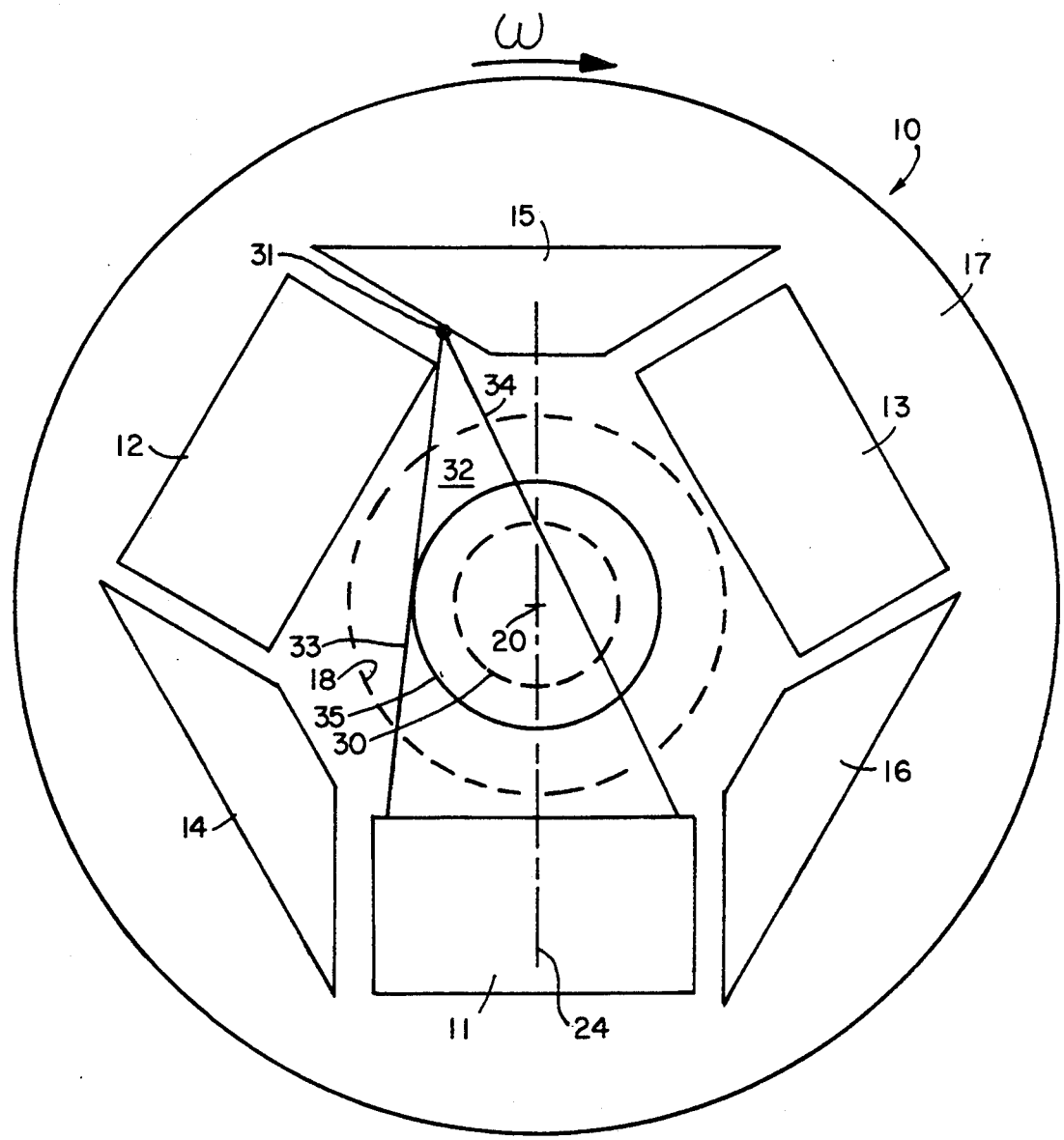
FIG. 2 depicts, in schematic form, a three-head single photon emission computed tomographic imaging apparatus with one embodiment of attenuation apparatus constructed in accordance with this invention.
Figure 3:
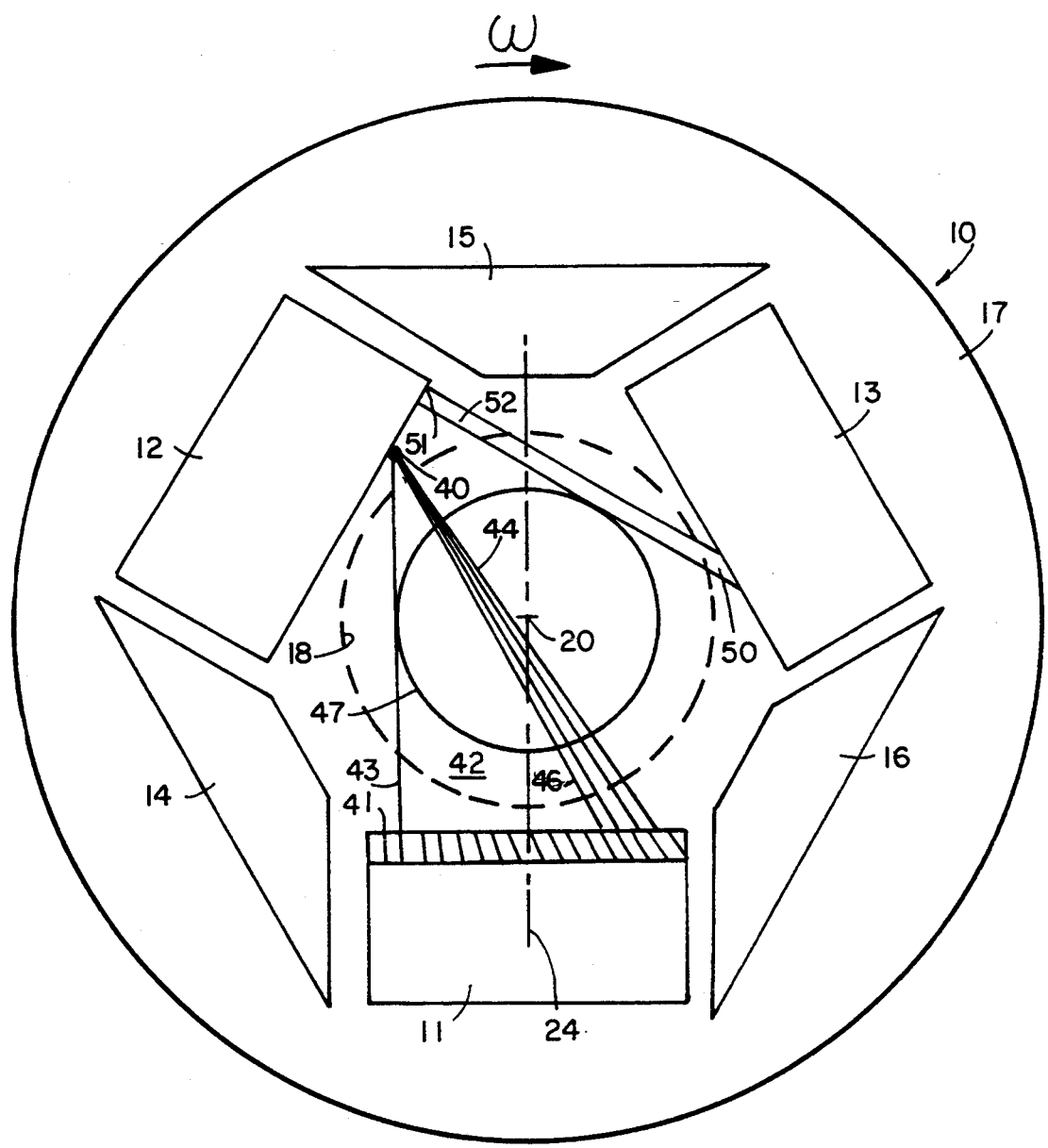
FIG. 3 depicts, in schematic form, a three-head single photon emission computed tomographic imaging apparatus with another embodiment of attenuation apparatus constructed in accordance with this invention.

FIG. 1 depicts the basic elements of a single photon emission computed tomographic (SPECT) apparatus constructed with a prior art radiation source such as shown in U.S. Pat. Nos. 5,210,421 and 5,075,554. Like reference numerals define like components of that apparatus throughout FIGS. 1 through 3. That is, each of FIGS. 1 through 3 depicts a three-headed SPECT gantry 10 with discrete detector heads 11, 12 and 13. Blocks 14, 15 and 16 represent mechanical control and driver systems associated with the heads, typically for changing the radial position of the heads. As shown, the gantry 10 typically carries these systems between the heads on a support 17. For example, the support plate 17 carries the systems in block 14 between the detector heads 11 and 12.

Referring specifically to FIG. 1, other systems, that are known in the art but are not shown in the figures, rotate the support plate 17 with a velocity ω to define a field of view represented by a dashed circle 18 about a central axis 20. The field of view 18 lies in the plane of FIG. 1 while the axis 20 is normal to that plane (i.e., at right angles to the plane of the support plate 17). A table (also not shown) supports a patient proximate the axis 20 and within the field of view 18 as represented by an object 21.

In accordance with prior art attenuation apparatus in FIG. 1, one detector head 11 includes a collimator 22 for defining a number of flight paths that will allow photons from the object 21 to reach photon detectors in the head 11. The collimator has a focal point located across the field of view. The support plate 17 carries an attenuation radiation source 23 at that focal point located on a diameter 24 through the center 20 of the field of view 18 and intersecting the head 11 at its midpoint. Lines 25 and 26 from the radiation source 23 to the opposite effective edges of the detector 11 (i.e., the left and right effective edges in FIG. 1) define the radiation fan 27 for the attenuation source 23. In this embodiment, therefore, the radiation fan 27 defines an isosceles triangle having a base at the detector 10 and an apex at the radiation source 23.

As the support plate 17 rotates, this radiation fan 27 provides full sampling through a circular attenuation field of view 30. By inspection, this attenuation field of view 30 is considerably smaller than both the emission imaging field of view 18 and the object 21, particularly when the object 21 is a human torso. In one specific apparatus with an imaging field of view 18 having a diameter of about 40 cm., the attenuation field of view 30 is about 21 cm. In lung and other applications the organ of interest may itself be greater than 21 cm. or may be off center such that accurate attenuation data can not be obtained by fully sampling even a specific region of interest.

FIG. 2 discloses a modification of the apparatus shown in FIG. 1 whereby a radiation source 31 produces an asymmetrical radiation fan 32 generally across the emission image field of view 18. In this embodiment the support plate 17 carries the radiation source 31 intermediate the detector head 12 and the mechanical control and driver systems 15. The radiation source 31 still lies across the field of view 18 from the detector 11, but is displaced by approximately one half the detector width from the diameter 24. Consequently a line 33 between the radiation source 31 and one edge of the detector 11 (i.e., the left edge in FIG. 2). forms a substantially right angle with the plane of the detector head 11. A line 34 defines the other boundary of the radiation fan 32 and extends between the radiation source 31 and the other effective edge of the detector head 11 (i.e., the right edge in FIG. 2).

When the support 17 rotates, the radiation fan 32 defines an attenuation field of view 35 that is circular and that has a greater diameter than the attenuation field of view 30, shown as a dashed circle in FIG. 2 and provided by the apparatus shown in FIG. 1. Thus, offsetting the location of the radiation source 31 and producing an asymmetrical radiation fan increases the attenuation field of view. When applied to the embodiment shown in FIGS. 1 and 2, this relocation of the radiation source 31 increases the attenuation field of view 18 from about 21 cm to an attenuation field of view 35 having a diameter of about 35 cm. This attenuation field of view will encompass lungs and other organs of interest in a majority of patients. Thus, this approach provides better and more even sampling for attenuation data of the entire field of view.

It is possible to implement this system in two alternatives. In one, the detector 11 may include a conventional dual energy detector and collimator thereby to allow the simultaneous receipt of data concerning both an emission image and a transmission image. The detector head 11 may act as a single energy detector dedicated for receiving photons from the radiation source 31 and rely on the emission data collected by the detector heads 12 and 13 for producing the resulting image. It is also possible to shutter the radiation source 31 thereby to effectively enable control the use of the transmission source 31 such that the transmission image can be obtained sequentially before the administration of the radionuclide tracer compound. Alternatively, the attenuation data can be obtained immediately after the emission scan data is obtained if the radiation from the attenuation source is much greater than from the emission radionuclide. When the attenuation data will be obtained without significant scatter in the object, it is also possible to obtain the attenuation data without a collimator in any of the foregoing alternatives.

FIG. 3 discloses a three-head SPECT system utilizing alternate attenuation apparatus in accordance with this invention. In this embodiment the plate 17 supports a radiation source 40 proximate the face of the detector head 12. A collimator 41, located on the detector head 11 defines an asymmetrical radiation fan 42 having a focal point at the radiation source 40. A line 43 represents a left-most flight path and a line 44 a right-most flight path between the radiation source 40 and the detector 41. Additional flight paths received at the detector 11 are depicted in part by lines 46.

The rotation of the support plate 17 therefore produces an attenuation field of view 47 that is greater than the attenuation field of view 35 produced by the apparatus in FIG. 2. Depending on the specific location of the radiation source 40, the field of view can correspond to or exceed a standard emission imaging field of view. In one particular example, corresponding to the apparatus described in FIGS. 1 and 2, the attenuation field of view can even exceed the imaging field of view 18.

If the field of view produced by the radiation source in FIG. 2 or the radiation source 40 in FIG. 3 is still insufficient, it is possible to add an auxiliary radiation source as, for example, at one edge of a head 13 directed to a section 51 of the detectors 12. This produces a narrow attenuation radiation beam 52 that can cover, for example, the annular area between the attenuation field of view 35 and the emission field of view 18. Alternatively, when applied at FIG. 2 this can increase is from the attenuation field of view 35 to the attenuation field of view 47.

As previously indicated, the detector heads 11, 12 and 13 could be constructed with dual energy photon detectors to obtain the emission scan and attenuation scan information simultaneously. Alternatively, the emission scan could be obtained utilizing detector heads 11, 12 and 13 and then the attenuation scan could be obtained using the radiation source 31 or 40 and the detector 11 and radiation source 50 and detector head 12 immediately after the emission data were obtained. Finally the detector 11 may or may not include a special collimator such as collimator 41 shown in FIG. 3 depending on the degree of scatter that might be encountered.

This invention has been disclosed in terms of certain embodiments. It will be apparent that many modifications can be made to the disclosed apparatus without departing from the invention. For example, each of the radiation sources may also include a source collimator to assist in defining a radiation fan. In addition each of the figures depicts an attenuation source used in a SPECT imaging apparatus characterized by three discrete heads. It will also be apparent that the attenuation source is equally applicable to radionuclide emission imaging apparatus including continuous detector rings. Therefore, it is the intent of the appended claims to cover all such variations and modifications as come within the true spirit and scope of this invention.

What is claimed as new and desired to be secured by Letters Patent of the United States is:

1. In radionuclide emission tomography apparatus for producing a tomographic image based upon the distribution of a photon emitting tracer in an object located within a predetermined field of view of the apparatus, the improvement of attenuation apparatus for obtaining attenuation data comprising:

A. detector means located outside the field of view for detecting the arrival of photons thereat and the distribution of photons thereat, B. photon source means located across and outside the field of view from said detector means and displaced from a diameter of the field of view that intersects the center of said detector means for directing photons across the field of view toward said detector means in a diverging pattern to define an asymmetrical radiation fan therebetween and a corresponding attenuation field of view.

2. Attenuation apparatus as recited in claim 1 additionally comprising a second photon source means located remotely from said first photon source means and additional detector means for producing attenuation data for a second attenuation field of view such that said attenuation field of view and said second attenuation field of view define an enlarged attenuation field of view.

3. Attenuation apparatus as recited in claim 2 wherein said tomographic apparatus includes rotatable means for supporting said detector means and said photon source means.

4. Attenuation apparatus as recited in claim 3 wherein said detector means includes asymmetrical fan collimator means for defining an asymmetrical field having a focal point and wherein said photon source means is located at the focal point.

5. Attenuation apparatus as recited in claim 2 further comprising collimator means proximate said detector means for defining an asymmetrical radiation fan with a focal point at said photon source means corresponding to the asymmetrical radiation fan from said photon source means.

6. Attenuation apparatus as recited in claim 1 wherein said tomographic apparatus is characterized by discrete photon detectors equiangularly spaced about the predetermined field of view and characterized by a finite width, said detector means comprising one of said discrete photon detectors and said photon source means being displaced from the diameter of the field of view that intersects the center of said one photon detector by a distance corresponding to one-half said finite width.

7. Attenuation apparatus as recited in claim 1 wherein said tomographic apparatus includes rotatable means for supporting said detector means and said photon source means.

8. Attenuation apparatus as recited in claim 7 wherein said tomographic apparatus is characterized by discrete photon detectors equiangularly spaced about the predetermined field of view and characterized by a finite width, said detector means comprising one of said discrete photon detectors and said photon source means being located across and outside the field of view from said one photon detector and displaced from a diameter of the field of view that intersects the center of said one photon detector by a distance corresponding to one-half said finite width.

9. Attenuation apparatus as recited in claim 8 wherein one photon detector includes asymmetrical fan collimator means for defining an asymmetrical field having a focal point and wherein said photon source means is located at the focal point.

10. Attenuation apparatus as recited in claim 8 wherein said photon source means is constituted by a collimated photon source for limiting the radiation therefrom to substantially the asymmetrical radiation fan defined between said one photon detector and said photon source.

11. Attenuation apparatus as recited in claim 8 further comprising collimator means proximate said one photon detector defining an asymmetrical radiation fan with a focal point at said photon source means corresponding to the asymmetrical radiation fan from said photon source means.

12. Attenuation apparatus as recited in claim 1 wherein said detector means includes asymmetrical fan collimator means for defining an asymmetrical field having a focal point and wherein said photon source means is located at the focal point.

13. Attenuation apparatus as recited in claim 1 wherein said photon source means is constituted by a collimated photon source for limiting the radiation therefrom to substantially the asymmetrical radiation fan defined from said detector means to said photon source.

14. Attenuation apparatus as recited in claim 13 additionally comprising a second photon source means located remotely from said first photon source means and additional detector means for producing attenuation data for a second attenuation field of view such that said attenuation field of view and said second attenuation define an enlarged attenuation field of view.

15. Attenuation apparatus as recited in claim 13 wherein said tomographic apparatus is characterized by discrete photon detectors equiangularly spaced about the predetermined field of view and characterized by a finite width, said detector means comprising one of said discrete photon detectors and said photon source means being located across and outside the field of view from said one photon detector and displaced from a diameter of the field of view that intersects the center of said one photon detector by a distance corresponding to one-half said finite width.

16. Attenuation apparatus as recited in claim 1 further comprising collimator means proximate said detector means for defining an asymmetrical radiation fan with a focal point at said photon source means corresponding to the asymmetrical radiation fan from said photon source means.

17. A method for providing an attenuation field of view in a radionuclide emission tomography apparatus that produces a tomographic image based upon the distribution of a photon emitting tracer in an object located within a predetermined field of view of the apparatus, said method comprising the steps of:

A. directing radiation from a radiation source positioned outside the predetermined field of view across the field of view in a diverging pattern from a focal point;

B. detecting the distribution of the diverging radiation pattern passing through the field of view by a detector positioned outside the predetermined field of view such that the pattern defines an asymmetric radiation fan from the radiation source through the field of view and to the detector; and C. rotating a support carrying the detector and the radiation source to produce the attenuation field of view.

18. A method as recited in claim 17 wherein the radiation source produces photons and said method further comprises the step of collimating at the detector the photons incident on the detector.

19. A method as recited in claim 17 further comprising the steps of directing a radiation beam across the field of view from a second radiation source carried by the support and detecting the distribution of the radiation in the radiation beam by a second detector carried by the support and positioned in the second radiation beam such that said step of rotating produces a second attenuation field of view such that the attenuation field of view and the second attenuation field of view define an enlarged field of view.

20. A method as recited in claim 17 wherein said step of directing further includes collimating the diverging pattern of radiation so as limit the pattern to the asymmetrical radiation fan.

* * * * *